United States Patent [19]

Kompis et al.

[11] 4,191,758
[45] Mar. 4, 1980

[54] BENZYLPYRIMIDINES

[75] Inventors: Ivan Kompis, Oberwil; Alexander E. Wick, Riehen, both of Switzerland

[73] Assignee: Hoffmann-La Roche Inc., Nutley, N.J.

[21] Appl. No.: 900,358

[22] Filed: Apr. 26, 1978

[30] Foreign Application Priority Data

May 5, 1977 [LU] Luxembourg .................... 77268

[51] Int. Cl.$^2$ .................. A61K 31/505; C07D 239/48
[52] U.S. Cl. .................................. 424/229; 424/251; 544/325; 260/465 F; 260/599
[58] Field of Search ............... 544/325; 424/229, 251

[56] References Cited
U.S. PATENT DOCUMENTS

| | | | |
|---|---|---|---|
| 3,985,876 | 10/1976 | Hazlett et al. | 424/228 |
| 3,996,356 | 12/1976 | Grunberg | 424/251 |
| 4,033,962 | 7/1977 | Rosen | 424/251 |

FOREIGN PATENT DOCUMENTS 1388213  3/1975  United Kingdom .................... 544/325

Primary Examiner—Paul M. Coughlan, Jr.
Attorney, Agent, or Firm—Jon S. Saxe; George M. Gould; Peter R. Shearer

[57] ABSTRACT

Benzylpyrimidines of the formula

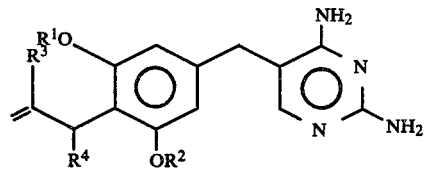

wherein $R^1$ and $R^2$, independently, are $C_{1-3}$-alkyl, and $R^3$ and $R^4$, independently, are hydrogen or methyl, and physiologically acceptable acid addition salts thereof, are described. The compounds of formula I are useful as antibacterial agents and as potentiators of sulfonamides.

12 Claims, No Drawings

BENZYLPYRIMIDINES

BRIEF SUMMARY OF THE INVENTION

The invention relates to compounds characterized by the formula

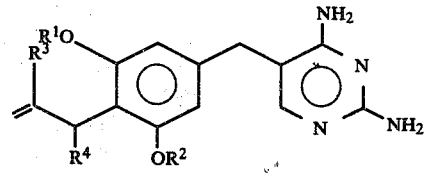

wherein $R^1$ and $R^2$, independently, are $C_{1-3}$-alkyl, and $R^3$ and $R^4$, independently, are hydrogen or methyl, and physiologically acceptable acid addition salts thereof.

In another aspect, the invention relates to pharmaceutical compositions which contain compounds of formula I.

In yet another aspect, the invention relates to intermediates for the preparation of the compounds of formula I.

DETAILED DESCRIPTION OF THE INVENTION

The benzylpyrimidines of the invention are compounds of the formula

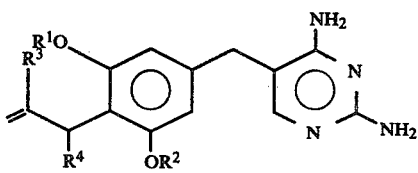

wherein $R^1$ and $R^2$, independently, are $C_{1-3}$-alkyl, and $R^3$ and $R^4$, independently, are hydrogen or methyl, or a physiologically acceptable acid addition salt thereof.

As used herein, the $C_{1-3}$-alkyl groups are methyl, ethyl, propyl and isopropyl. Preferred compounds of formula I are, on the one hand, those in which $R^1$ and $R^2$ are the same and each is methyl or ethyl, and, on the other hand, those in which $R^3$ and $R^4$ are hydrogen. Especially preferred is 5-(4-allyl-3,5-dimethoxybenzyl)-2,4-diaminopyrimidine, and its acid addition salts.

In accordance with the present invention, the benzylpyrimidines, that is, the compounds of formula I and their salts, are prepared by (a) etherifying the hydroxy group in a compound of the formula

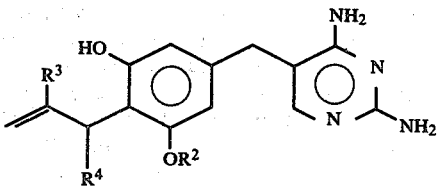

wherein $R^2$, $R^3$ and $R^4$ are as previously described, to a $C_{1-3}$-alkoxy group, or (b) reacting a compound of the formula

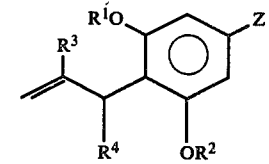

wherein $R^1$, $R^2$, $R^3$ and $R^4$ are as previously described, Z is a group of the formula $-CH_2-CH(CN)-CH(OR^7)_2$ or $-CH_2-C(=CHY)CN$ in which $R^7$ is $C_{1-4}$-alkyl or both $R^7$'s, taken together, are $C_{1-4}$-alkylene and Y is a leaving group, with guanidine or a guanidine salt, and, if desired, converting a compound of formula I so obtained into an acid addition salt, if desired.

As used herein, $C_{1-4}$-alkyl and $C_{1-4}$-alkylene groups are straight-chain or branched-chain groups containing 1–4 carbon atoms. Exemplary of $C_{1-4}$-alkyl are methyl, ethyl, propyl, isopropyl, butyl and tert. butyl and exemplary of $C_{1-4}$-alkylene are methylene, ethylene and 2,3-butylene.

According to process embodiment (a) of the present invention, the hydroxy group in a compound of formula II is etherified. This etherification can be carried out in a known manner, for example, by reaction with an alkylating agent of the formula $R^1X$ in which $R^1$ is $C_{1-3}$-alkyl and X is, for example, chlorine, bromine or iodine. This embodiment of the process is especially suitable for the preparation of compounds of formula I wherein $R^1$ and $R^2$ are different $C_{1-3}$-alkyl groups.

The starting materials of formula II can be prepared in accordance with Formula Scheme I hereinafter from compounds of formula VI using generally known reactions.

A compound of formula V can be obtained, for example, very readily by partially dealkylating a 3,5-dialkoxybenzyl compound of formula VI, preferably by partially demethylating a 3,5-dimethoxybenzyl compound, with excess sodium ethylmercaptide in dimethylformamide. A compound of formula V is then reacted with an alkylating agent of the formula $H_2C=C(R^4)-CH(R^3)X$, wherein $R^3$, $R^4$ and X are as previously described, to given an allyl ether of formula IV which is finally subjected to a Claisen rearrangement to give a starting material of formula II.

Formula Scheme I

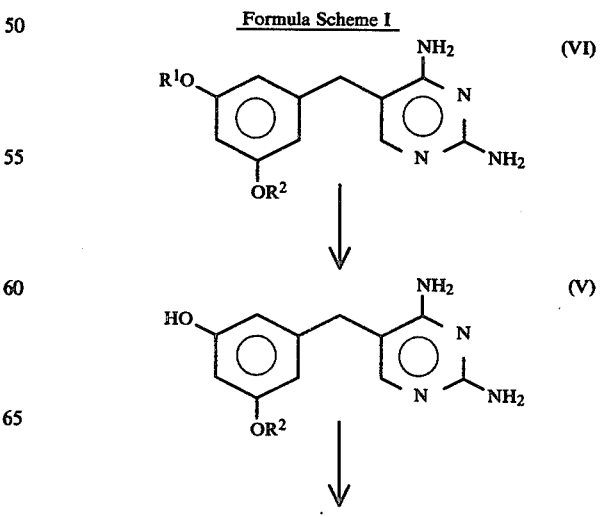

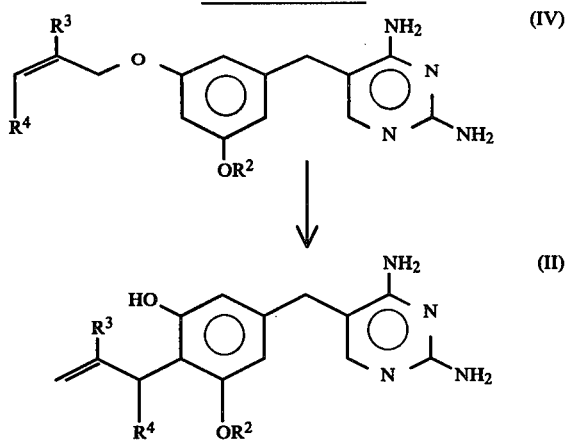

piperidino, piperazino, morpholino, or arylamino, for example, optionally substituted anilino, or naphthylamino. Especially preferred is anilino, the phenyl ring of which can optionally carry one or more halogen, alkyl or alkoxy substituents.

The starting materials of formula III, that is, the compounds of formulas III-1 and III-2 hereinafter, can be prepared in a known manner in accordance with Formula Scheme II hereinafter, for example, from compounds of formula XI by esterification, conveniently to the tert.-butyl ester, etherification of the hydroxy group with a suitable allyl halide, Claisen rearrangement, reduction of the ester group to the aldehyde group and condensation of a resulting compound of formula VII with a β-substituted-propionitrile of the formula NC—CH$_2$—CH$_2$OR$^7$, with subsequent addition of an alkanol of the formula R$^7$OH, or NC—CH$_2$—CH$_2$Y. The compounds of formulas III, that is, the compounds of formulas III-1 and III-2, and VII are novel and also form part of the present invention.

According to process embodiment (b) of the present invention, a compound of formula III is reacted with guanidine or a guanidine salt. The reaction can be carried out in a known manner, for example, in an organic solvent, such as, an alkanol, for example, methanol or ethanol; dimethylformamide; dimethylsulfoxide; or N-methylpyrazolone, at a temperature in the range of from about 25° C. to 200° C., preferably in the range of from about 50° C. to 170° C. Examples of guanidine salts which can be used are the carbonate and the hydrochloride. Examples of leaving groups denoted by Y in compounds of formula III-2, hereinafter, are alkoxy, such as methoxy, ethoxy, propoxy or the like, alkylthio, and aliphatic, aromatic or heterocyclic amino groups, such as alkylamino, benzylamino, dialkylamino, pyrrolidino, To prepare acid addition salts, especially those salts which can be used in pharmaceutical preparations, that is, physiologically or pharmaceutically acceptable salts, there come into consideration inorganic and organic acids which are customarily used for this purpose, such as hydrochloric acid, sulfuric acid, phosphoric acid, formic acid, acetic acid, oxalic acid, tartaric acid, maleic acid, benzoic acid, succinic acid, fumaric acid, levulinic acid, salicyclic acid, citric acid, isocitric acid, adipic acid, lactic acid, α-ketoglutaric acid, malic acid, malonic acid, glyceric acid, mevalonic acid, glucuronic acid, neuraminic acid, glutaric acid, aspartic acid, gluconic acid, mandelic acid, ascorbic acid, lactobionic acid, glucoheptonic acid, glutamic acid, nicotinic acid, pantothenic acid, folic acid, adenylic acid, geranylic acid, cytidylic acid, inosic acid, or the like.

The compounds of formula I have antibacterial activity. They inhibit the bacterial dihydrofolic acid reductase (DHFR) and, moreover, potentiate the activity of sulfonamides and other dihydrofolic acid synthetase inhibitors. Accordingly, the compounds of formula I are useful as antibacterials agents and as potentiators of the active sulfonamides. Examples of sulfonamides which are potentiated by the compounds provided by the present invention are sulfadiazine, sulfadimethoxine, sulfadoxine, sulfamethoxazole, sulfisoxazole, sulfamoxole, 3-sulfanilamido-4,5-dimethylisoxazole, sulfalene, sulfamerazine, sulfameter, sulfamethazine and 6-methoxy-4-sulfanilamidopyrimidine. They are qualitatively comparable with structurally analogous benzylpyrimidines. Quantitatively, however, compared with known compounds, the compounds provided by the present invention are characterized by lower 50% inhibitory concentrations of the bacterial DHFR, for example, in the case of E. coli. For 5-(4-allyl-3,5-dimethoxybenzyl)-2,4-diaminopyrimidine this value is, for example, $0.5 \cdot 10^{-8}$ M/l compared with $0.9 \cdot 10^{-8}$ M/l for trimethoprim, while the $CD_{50}$ (mg/kg) of 5-(4-allyl-3,5-dimethoxybenzyl)-2,4-diaminopyrimidine plus sulfamethoxazole (1:1 w/w) is 2.4 against Streptococcus pyogenes compared with 6.6 for trimethoprim plus sulfamethoxazole (1:1 w/w).

The benzylpyrimidines provided by the invention can be used in the form of pharmaceutical preparations, having direct or delayed liberation of the active ingredient, in association with a compatible pharmaceutical carrier material. This carrier material can be an organic or inorganic inert carrier material suitable for oral, rectal or parenteral administration, for example, water, gelatin, gum arabic, lactose, starch, magnesium stearate, talc, vegetable oils, polyalkyleneglycols, petroleum jelly, or the like. The pharmaceutical preparations can be made up in a solid form, for example, as tablets, dragees, suppositories or capsules, in a semi-solid form, for example, as salves, or in a liquid form, for example, as solutions, suspensions or emulsions. The pharmaceutical preparations may be sterilized and/or may contain additional adjuvants, such as preserving, stabilizing, wetting or emulsifying agents, flavor-improving agents, salts for varying the osmotic pressure or buffer substances. The pharmaceutical preparations can be prepared in a known manner.

In pharmaceutical preparations containing a benzylpyrimidine of this invention and a sulfonamide, the weight ratio of the two components to one another can vary within wide limits. The ratio can be in the range of from 1:40 to 10:1, and preferably in the range of from 1:5 to 5:1. A tablet can contain, for example, 80 to 400 mg. of a compound of formula I and 400-80 mg. of a sulfonamide. In the case of pharmaceutical preparations containing a compound of formula I as the sole active ingredient 100-1000 mg. can be considered as the guideline for a single dose, which, depending on requirements, can be administered once daily or several times daily.

The Examples which follow further illustrate the invention.

EXAMPLE 1

Preparation of 5-(4-allyl-3,5-dimethoxybenzyl)-2,4-diaminopyrimidine

A mixture of 1.43 g. of 6-allyl-α-(2,4-diamino-5-pyrimidyl)-5-methoxy-m-cresol, 5 ml. of 1-N potassium hydroxide and 300 ml. of 40% aqueous methanol was treated with 0.32 ml. of methyl iodide and stirred at room temperature for 48 hours. The methanol was removed by distillation and the residue was extracted with ethyl acetate. Working-up of the ethyl acetate extract yielded 5-(4-allyl-3,5-dimethoxybenzyl)-2,4-diaminopyrimidine of melting point 185°-187° C. (from methanol) in a yield of 75%.

The starting material was prepared as follows:

A solution of 32.2 g. of ethylmercaptan in 310 ml. of dimethylformamide was added dropwise with cooling and nitrogen gasification to a suspension of 25 g. of 50% sodium hydride in 310 ml. of dimethylformamide. The mixture was subsequently treated with a solution of 27 g. of 2,4-diamino-5-(3,5-dimethoxybenzyl)pyrimidine in 310 ml. of dimethylformamide, stirred at 100° C. for 17 hours, cooled down to room temperature and concentrated under a high vacuum. The residue, dissolved in a small amount of water, was filtered, the filtrate was extracted three times with 50 ml. of benzene each time and the aqueous phase was adjusted to pH 4-5 with concentrated hydrochloric acid while cooling with ice-water. Subsequently, it was brought to pH 9 with concentrated ammonia and the precipitated product, 23.3 g. of α-(2,4-diamino-5-pyrimidyl)-5-methoxy-m-cresol of melting point 254°-255° C. (from methanol) was isolated.

A solution of α-(2,4-diamino-5-pyrimidyl)-5-methoxy-m-cresol in 180 ml. of dimethylformamide was added dropwise with stirring and nitrogen gasification to a suspension of 4.3 g. of 50% sodium hydride in 45 ml. of dimethylformamide. After 30 minutes, the mixture was treated dropwise with 10.8 g. of allyl bromide and stirred at room temperature for 1 hour. The solution was concentrated to dryness at 60° C. under a high vacuum, the residue was suspended in a small amount of water, washed with benzene and extracted with ethyl acetate. Working-up of the organic phase and recrystallization of the crude product from ethyl acetate/petroleum ether yielded 20.7 g. of 5-(3-allyl-5-methoxybenzyl)-2,4-diaminopyrimidine of melting point 246°-248° C.

A suspension of 15.5 g. of 5-(3-allyl-5-methoxybenzyl)-2,4-diaminopyrimidine in 31 ml. of diethylaniline was warmed to 215° C. for 75 minutes with stirring and nitrogen gasification. The resulting solution was cooled down, treated with 35 ml. of n-heptane and stirred at room temperature for 30 minutes. The precipitated crude product, a mixture of 4-allyl- and 6-allyl-α-(2,4-diamino-5-pyrimidyl)-5-methoxy-m-cresol, was removed by filtration under suction, washed with ether and stirred with 60 ml. of 1-N sodium hydroxide for 1 hour. The residue, the 6-allyl compound, was removed by filtration under suction, dissolved in 10 ml. of 1-N hydrochloric acid and again precipitated by the addition of concentrated ammonia up to pH 8. There were obtained 1.85 g. of 6-allyl-α-(2,4-diamino-5-pyrimidyl)-5-methoxy-m-cresol, having a melting point of 240°-243° C.

EXAMPLE 2

Preparation of 5-(4-allyl-3,5-dimethoxybenzyl)-2,4-diaminopyrimidine 13.6 G. of dimethylsulfate were added dropwise to a solution of 14.0 g. of a mixture of 4-allyl- and 6-allyl-α-(2,4-diamino-5-pyrimidyl)-5-methoxy-m-cresol, obtained as described in Example 1, in 98 ml. of 1-N sodium hydroxide and 245 ml. of methanol. The mixture was stirred at room temperature for 18 hours, the methanol was removed, the residue was taken up in 200 ml. of water and exhaustively extracted with ethyl acetate. The organic extract was washed with a small amount of concentrated ammonia and water, dried over magnesium sulfate and concentrated to dryness. The residue was chromatographed on silica gel with chloroform/propanol/concentrated ammonia (80:2:1, v/v/v). On the basis of the different Rf-values, the undesired 5-(2-allyl-3,5-dimethoxybenzyl)-2,4-diaminopyrimidine (Rf 0.6) could be separated from the 5-(4-allyl-3,5-dimethoxybenzyl)-2,4-diaminopyrimidine (Rf 0.5); melting point 185°–187° C. (from methanol).

The following Example illustrates a pharmaceutical preparation provided by the invention:

EXAMPLE

Tablets, each containing the following ingredients:

| | |
|---|---|
| 5-(4-allyl-3,5-dimethoxybenzyl)-2,4-diaminopyrimidine | 80.00 mg. |
| Pregelatinized starch | 12.50 mg. |
| Sodium carboxymethyl-starch | 12.50 mg. |
| Lactose (powdered) | 131.25 mg. |
| Maize starch | 12.50 mg. |
| Magnesium stearate | 1.25 mg. |
| | 250.00 mg. | were prepared by moist granulating a mixture of the aforementioned ingredients with the addition of water, drying the resulting granulate and pressing the dried granulate into tablets.

We claim:

1. A compound of the formula

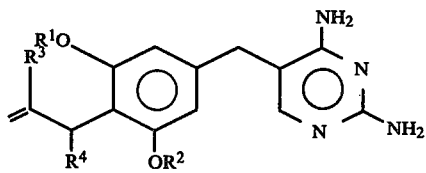

wherein $R^1$ and $R^2$, independently, are $C_{1-3}$-alkyl, and $R^3$ and $R^4$, independently, are hydrogen or methyl, or a physiologically acceptable acid addition salt thereof.

2. A compound in accordance with claim 1, wherein $R^1$ and $R^2$ are each the same $C_{1-3}$-alkyl.

3. A compound in accordance with claim 2, wherein $R^1$ and $R^2$ are methyl.

4. A compound in accordance with claim 2, wherein $R^1$ and $R^2$ are ethyl.

5. A compound in accordance with any one of claims 1 to 4 inclusive, wherein $R^3$ is hydrogen.

6. A compound in accordance with any one of claims 1 to 4 inclusive, wherein $R^3$ is methyl.

7. A compound in accordance with claim 2 wherein $R^4$ is hydrogen.

8. A compound in accordance with claim 2, wherein $R^4$ is methyl.

9. A compound in accordance with claim 1, 5-(4-allyl-3,5-dimethoxybenzyl)-2,4-diaminopyrimidine.

10. An antibacterial pharmaceutical composition comprising a compound of the formula

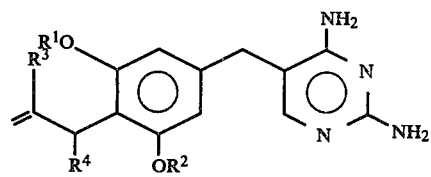

wherein $R^1$ and $R^2$, independently, are $C_{1-3}$-alkyl, and $R^3$ and $R^4$, independently, are hydrogen or methyl, or a physiologically acceptable acid addition salt thereof, an antibacterially active sulfonamide and a compatible pharmaceutical carrier material, said compound of formula I being present in an amount sufficient to potentiate the antibacterial activity of the sulfonamide.

11. An antibacterial pharmaceutical composition in accordance with claim 10 comprising a compound of the formula

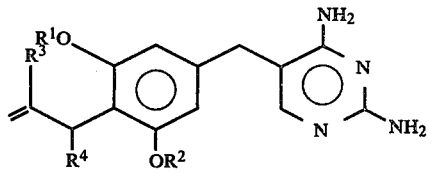

wherein $R^1$ and $R^2$, independently, are $C_{1-3}$-alkyl, and $R^3$ and $R^4$, independently, are hydrogen or methyl, or a physiologically acceptable acid addition salt thereof, an antibacterially active sulfonamide and a compatible pharmaceutical carrier material, the ratio of said compound of formula I to said antibacterially active sulfonamide in the composition being from 1:40 to 10:1.

12. An antibacterial pharmaceutical composition in accordance with claim 11, wherein the ratio of said compound of formula I to said antibacterially active sulfonamide is from 1:5 to 5:1.